(12) United States Patent
Hilbrink et al.

(10) Patent No.: US 9,144,515 B2
(45) Date of Patent: Sep. 29, 2015

(54) DEVICE AND METHOD FOR ADMINISTERING A LIQUID DROP-BY-DROP

(75) Inventors: Hubertus E. Hilbrink, Apeldoorn (NL); Johannes Van Der Heiden, Tilburg (NL); Leonardus H. M. Lammers, Hoofddorp (NL)

(73) Assignee: Sparkle Innovations B.V. (NL)

( * ) Notice: Subject to any disclaimer, the term of this patent is extended or adjusted under 35 U.S.C. 154(b) by 528 days.

(21) Appl. No.: 13/123,229

(22) PCT Filed: Oct. 7, 2009

(86) PCT No.: PCT/NL2009/050604
§ 371 (c)(1),
(2), (4) Date: Apr. 7, 2011

(87) PCT Pub. No.: WO2010/041941
PCT Pub. Date: Apr. 15, 2010

(65) Prior Publication Data
US 2011/0208138 A1 Aug. 25, 2011

(30) Foreign Application Priority Data

Oct. 7, 2008 (NL) ...................................... 1036024

(51) Int. Cl.
*A61J 1/00* (2006.01)
*A61F 9/00* (2006.01)
*A61M 35/00* (2006.01)

(52) U.S. Cl.
CPC ............ *A61F 9/0008* (2013.01); *A61M 35/003* (2013.01); *A61J 1/00* (2013.01)

(58) Field of Classification Search
CPC ............... A61J 1/035; A61J 1/16; A61J 3/00; A61M 5/00; A61M 5/145; B65D 77/06; B65D 83/00
USPC .......... 604/289, 290, 403–416; 424/447, 449; 206/570, 571; 222/95
See application file for complete search history.

(56) References Cited

U.S. PATENT DOCUMENTS

| 5,163,583 | A | 11/1992 | Whitworth |
| 2007/0191780 | A1 | 8/2007 | Modi |
| 2007/0270763 | A1* | 11/2007 | Tanner et al. .................. 604/232 |

FOREIGN PATENT DOCUMENTS

| GB | 2206794 | 1/1989 |
| WO | WO 2005/094742 | 10/2005 |
| WO | WO 2008/083209 | 7/2008 |

OTHER PUBLICATIONS

PCT Patent Application No. PCT/NL/2009/050804 filed Oct. 7, 2009 in the name of Hilbrink et al., International Search Report and Written Opinion mailed Mar. 18, 2010.

*Primary Examiner* — Melanie Hand
(74) *Attorney, Agent, or Firm* — Levine Bagade Han LLP

(57) ABSTRACT

The invention relates to a device for administering a liquid drop by drop. This administering device comprises a packaging filled with the liquid, an outflow channel with an administering opening, and means connected to the outflow channel for opening the packaging, wherein the opening means and the packaging are movable relative to each other. The device can have means for receiving the packaging, which receiving means can be adapted to fix the packaging, wherein the opening means are then movable relative to the receiving means. The opening means can conversely also be fixed relative to the receiving means, wherein the packaging is then movable in the receiving means. The opening means can be formed by a sharp outer end of the outflow channel. The invention further relates to a method for administering a liquid drop by drop, comprising the steps of:—supplying a packaging filled with liquid,—forming an opening in the packaging using opening means, and—connecting the opening to an outflow channel which has an administering opening, wherein the opening is formed by moving the opening means and the packaging relative to each other. The device and method according to the invention make it possible to press liquid per drop out of the packaging. Drops are formed here of a substantially constant volume and the quality thereof is guaranteed.

18 Claims, 5 Drawing Sheets

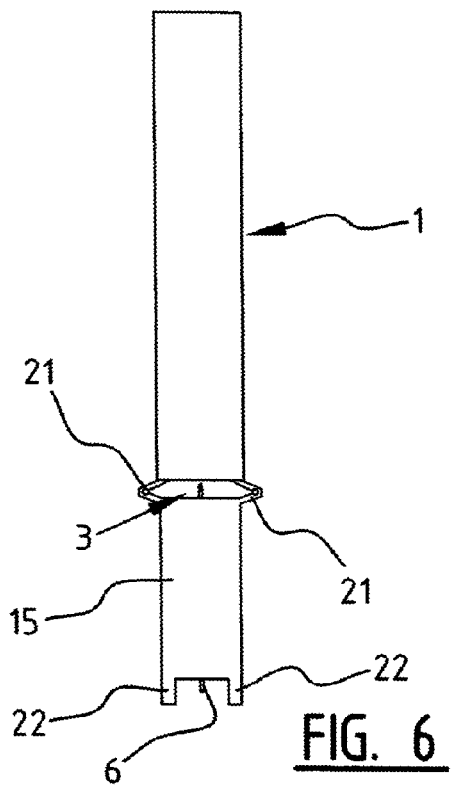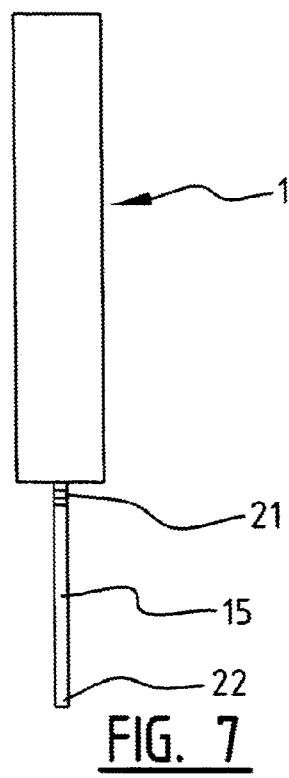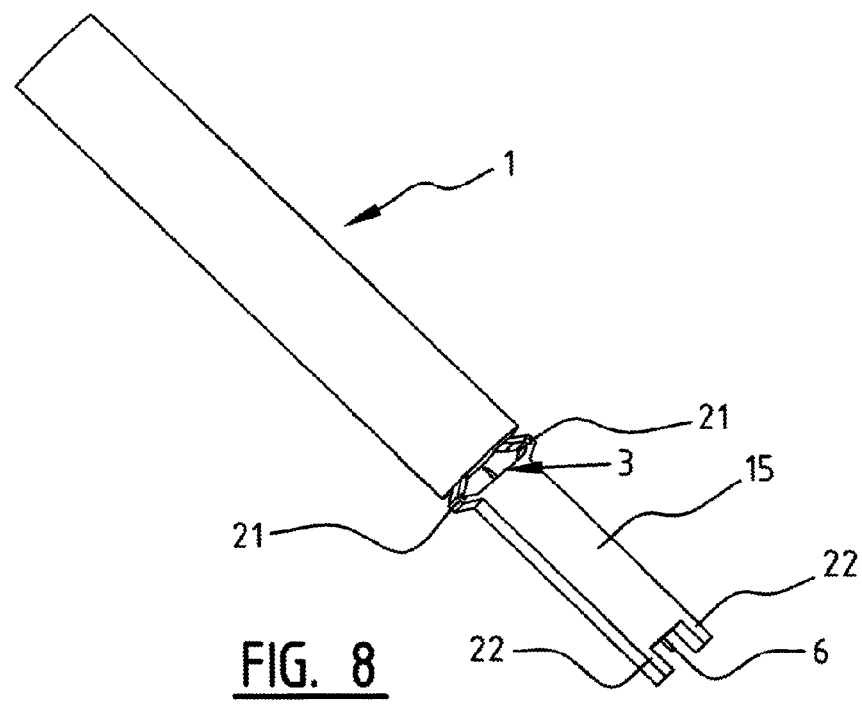

DEVICE AND METHOD FOR ADMINISTERING A LIQUID DROP-BY-DROP

Figure 1A:
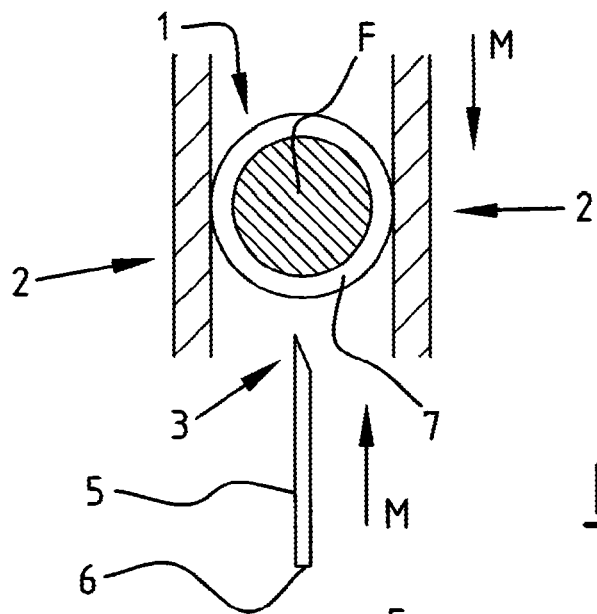

The invention relates to a device for administering a liquid drop by drop. The invention relates particularly to a device with which eye-drops can be administered in controlled manner with a reproducible volume and a guaranteed quality.

Devices known heretofore for administering eye-drops can be divided into two groups; droppers for multiple use and droppers for once-only use. "Multiple use" is understood to mean the use at different moments or points in time with long intervals. Conversely, "once-only use" is understood to mean the use at a determined moment or point in time. A plurality of eye-drops can here be delivered, optionally into both eyes of the user.

Administering devices for multiple use are provided with a relatively large container, often a glass bottle, in which is received a quantity of liquid sufficient for administering for some time at regular intervals. A dropper is mounted on the neck of this container. These administering devices have a number of drawbacks.

In view of their prolonged use the liquids in these devices thus often comprise preservatives which can be harmful to the eye. In addition, it is often not known when the device was taken into use, so that there is the risk of it being used for too long. In this case micro-organisms could grow in the liquid, despite the preservatives, which could result in eye infection and even blindness. The growth of micro-organisms is further enhanced by the liquid coming into contact with ambient air drawn in each time it is administered. Such large administering devices are moreover regularly used for different patients, which can result in cross-infection between these patients.

The known administering devices for multiple views dispense droplets whose size can vary quite considerably. These drops are in any case relatively large in proportion to the volume of tear-water in the eye. It is known from the literature (T. F. Patton, "Pharmacokinetic evidence for improved ophthalmic drug delivery by reduction of instilled volume", Journal of Pharmaceutical Sciences, 66(7), pp. 1058-1059, July 1977) that relatively small eye-drops can have a comparable therapeutic effect. Large drops have the drawback, among others, that apart of the excess liquid can be taken up directly into the blood through the tear-duct, whereby side-effects can be caused.

Administering devices for once-only use usually consist of a relatively small plastic container with an integrated dropper. Such devices for once-only use also have a number of drawbacks.

As a result of their small dimensions these devices thus provide hardly any space for the purpose of arranging thereon information relating for instance to use. The information must therefore be in relatively small print, whereby it will be hardly legible to the users, who will often have poor eyesight. Owing to their small dimensions these administering devices are also difficult to handle for patients who will often be somewhat older. While different aids have been proposed for improving handling of the small devices, these are not always found to be effective.

These small devices are further often intended to be opened by a cap being broken or torn off, the so-called "twist-off". The dimensions of the thus created administering opening are not always the same, and often too large, thereby resulting in large drops. The tear-off edge is also often of irregular form, whereby the drop size can vary considerably. In addition, the tear-off edge can result in damage to the eye.

Finally, the cap can often be re-placed in such administering devices for once-only use, whereby there is the risk of the device being used more than once. There is then once again the risk of infection of the liquid.

Known from the earlier document U.S. Pat. No. 5,163,583 is a cap having integrated therein a passage with spike which can be placed on a test tube with blood closed by a stopper with opening. The passage herein passes through the opening, whereby blood samples can be dripped onto a diagnostic plate by slightly pressing the cap and stopper, whereby a pump action is as it were generated.

The earlier documents WO 2008/083209, US 2007/0191780 and GB 2 206 794 describe different variants of injection devices with which an active substance can be injected through the skin into the body of a user. Present in each of these is a reservoir which is closed by a membrane and on which pressure is exerted from outside. Once this pressure is sufficiently great the membrane is pierced by a needle, after which the liquid is injected with force in the form of a jet into the body.

The invention now has for its object to provide an administering device of the above stated type wherein these drawbacks do not occur, or at least do so to lesser extent. This is achieved according to the invention with a device for dispensing a liquid drop by drop, comprising a packaging at least partially filled with the liquid, at least one outflow channel with an administering opening, and means connected to the at least one outflow channel for opening the packaging, wherein the opening means and the packaging are movable relative to each other. By making use of such a device for administering purposes the liquid can be received in a packaging which remains hermetically closed until the moment of administration. The danger of infection is thus avoided. By making use of opening means it is possible to dispense with a tear-off cap, so that the packaging can be easily opened without creating problematic torn edges.

To enable handling of the packaging, the device can be provided with means for receiving the packaging, which receiving means can be adapted to fix the packaging, in which case the opening means will be movable relative to the receiving means. The receiving means can here then form part of a frame and the opening means can be mounted movably in the frame.

Conversely, it is possible for the device to once again be provided with means for receiving the packaging, while the opening means are fixed relative to the receiving means and the packaging is movable in the receiving means. In this case the administering device can be provided with at least one displacing member engaging on the packaging and to be inserted into the receiving means.

Finally, it is of course also possible to envisage the opening means and the packaging both being movable, although this will usually result in a more complicated embodiment.

The opening means are preferably connected movably to the packaging. The administering device can then take a very simple form, since it need only provide resistance when the opening means and the packaging are moved toward each other. It is even possible to envisage the packaging and the opening means forming the whole administering device.

A structurally simple embodiment of the administering device with a small number of components is also achieved when the opening means are formed by a sharp outer end of the at least one outflow channel.

The packaging is preferably deformable and the administering device is provided with means for exerting pressure on the packaging, whereby the liquid drops can be pressed out of the packaging via the outflow channel to the administering opening. Owing to the deformable character of the packaging the drops can be dispensed without air having to be drawn in.

When the receiving means define a receiving space, the pressing means can comprise a movable or deformable wall part of the receiving space engaging on the packaging. When the packaging is placed in the receiving space the user can thus empty it by pressing on the outside of the device.

In order to develop some "feel" for administering, and so prevent a large quantity of liquid unintentionally being administered at one time, the device can be provided with means co-acting with the pressing means for generating a resistance.

The device is preferably further provided with means for temporary fixing of the pressing means. Such temporary fixation means prevent liquid flowing back to the packaging and ambient air being drawn in when the pressure is removed. This could after all result in contamination of the liquid.

The administering device can further have means for generating a start signal when the pressing means occupy a ready-to-use position, and means for generating an end signal when the pressing means have reached an end position. With these signals, which could be audible, visual and tactile, the user is warned on the one hand that exerting pressure on the device will result in drops being dispensed, and on the other that further exertion of pressure is pointless since a full dosage has been reached. The signals could simply take the form of an audible and feelable click at the beginning and end of administering. The device could also generate signals between the start and end signal to indicate the progress of the administration, for instance at each drop that is dispensed.

In order to prevent the packaging having to be wholly pressed together in order to drip a desired dosage of liquid therefrom, it is recommended that the content of the packaging is such that liquid remains therein when the pressing means reach an end position. A full dosage is thus guaranteed under all conditions, even when a user for instance sometimes allows a drop to fall wide of the eye.

When the administering device is provided with means for making the device unsuitable for further use, it is possible to prevent the administering device being used more than once, which would involve a risk of infection. This could be achieved for instance by enclosing the packaging permanently in the receiving means, although other solutions can also be envisaged, such as deforming the outflow channel, damaging a seal or label and the like.

In order to prevent contact and damage to the eye during administering of the drops the administering opening is preferably arranged countersunk in a surrounding part of the device. The administering device can in this case have indicator means for indicating the administering opening, so that the user can position this opening in simple manner over the eye.

The dimensions of the administering device are preferably considerably larger than those of the packaging so that it is easy to handle, even for older users. In this case the administering device can further be provided with means for receiving at least one information carrier with for instance information relating to the nature of the liquid and the use thereof, for which there would be no space on the packaging.

When the device has means for closing the administering opening, the opening means and the outflow channel are guaranteed to remain sterile until the device is used.

The administering opening and/or the outflow channel are preferably adapted to form drops with a volume of 1 to 50 µl, preferably 2 to 25 µl, more preferably 3 to 10 µl and most preferably 5 to 7 µl. According to the scientific literature, such small drops are highly effective. It should be remembered in this respect that the total quantity of liquid on a human eye amounts in general to about 7 µl, so that dispensing an eye-drop of 7 µl already results in a 1:1 dilution of the active substance present therein.

It is recommended here that the administering opening is defined by a tubular outer end of the outflow channel, the external diameter of which amounts to a maximum of several millimeters. The external diameter of the outflow channel more preferably even amounts to only 0.2 to 0.7 millimeters. The applicants have had the insight that the drop size is not so much related to the throughflow area of the channel through which the eye-drops are dispensed, but rather with the outer diameter thereof.

The invention further relates to a method for administering a liquid drop by drop from a packaging. According to the invention this method comprises the steps of receiving the packaging in receiving means, forming at least one opening in the packaging using opening means and connecting the at least one opening to at least one outflow channel which has an administering opening, wherein the opening is formed by moving the opening means and the packaging relative to each other. Liquid can thus be dripped in rapid and simple manner from a packaging which is closed hermetically until the moment of use.

In a first variant of the method according to the invention the packaging is fixed in the receiving means and the opening means are moved toward the packaging.

In another variant of the method the opening means are conversely fixed relative to the receiving means and the packaging is moved toward the opening means.

The packaging is preferably deformable and the liquid is pressed therefrom. The packaging can be placed for this purpose in a receiving space of the receiving means and the liquid can be pressed therefrom by exerting a pressing force on a movable or deformable wall part of the receiving space.

A well controllable delivery of the drops is achieved when substantially no pressure is exerted on the packaging during forming of the at least one opening.

It is further recommended that the liquid is pressed out of the packaging at a pressure of a maximum of 2 bar, and preferably a maximum of 1 bar. Such low pressures ensure that the liquid is dispensed in the form of individual drops.

Finally, the invention further relates to a combination of a packaging and opening means connected movably thereto, evidently intended for use in an administering device as described above.

Figure 1B:
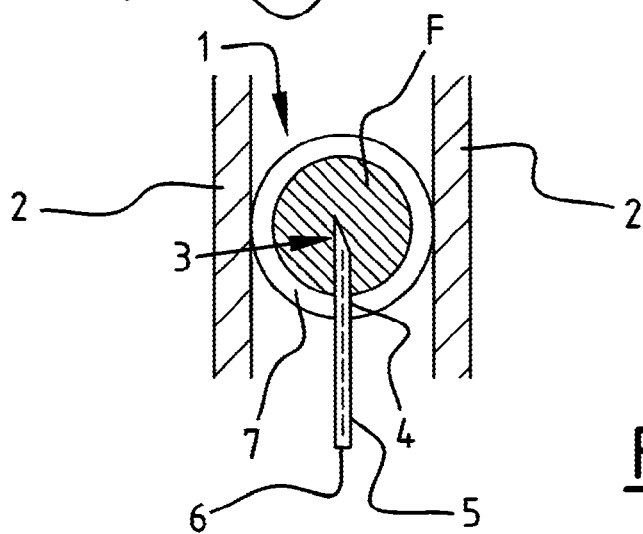
Figure 1C:
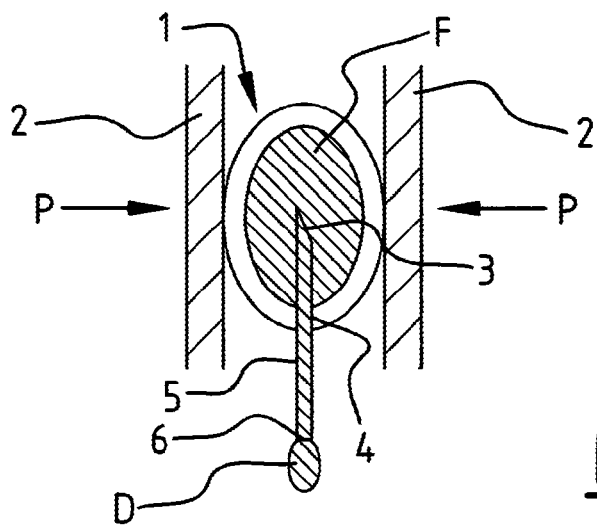
Figure 2:
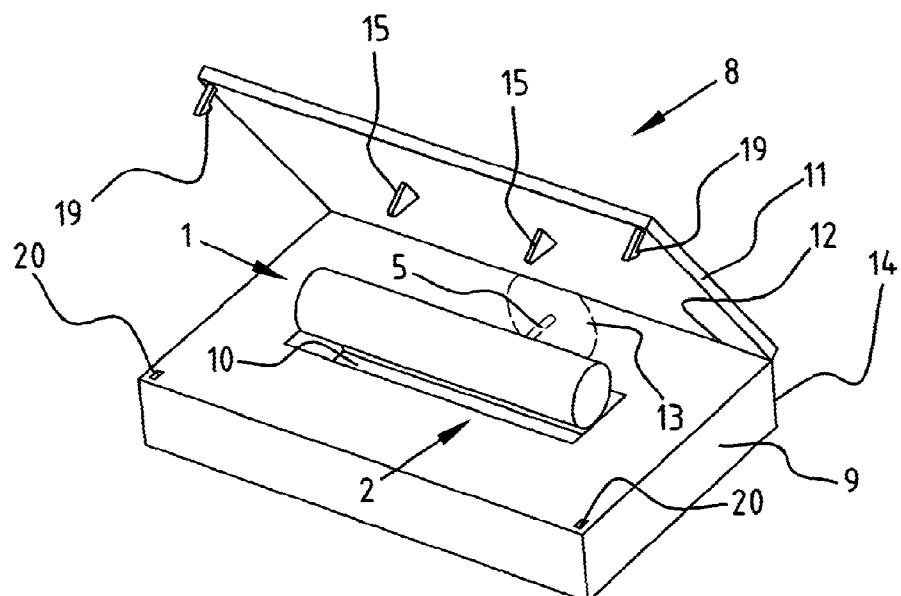
Figure 3:
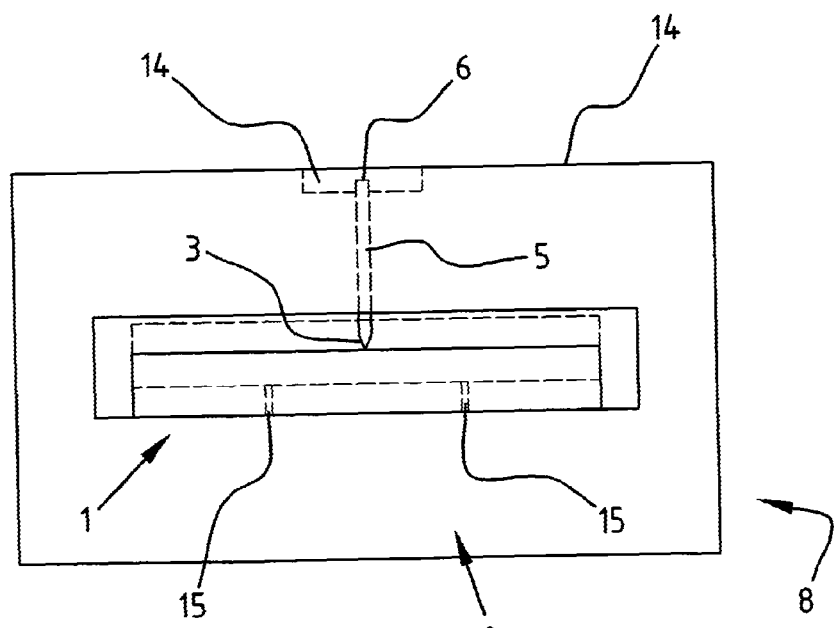
Figure 4:
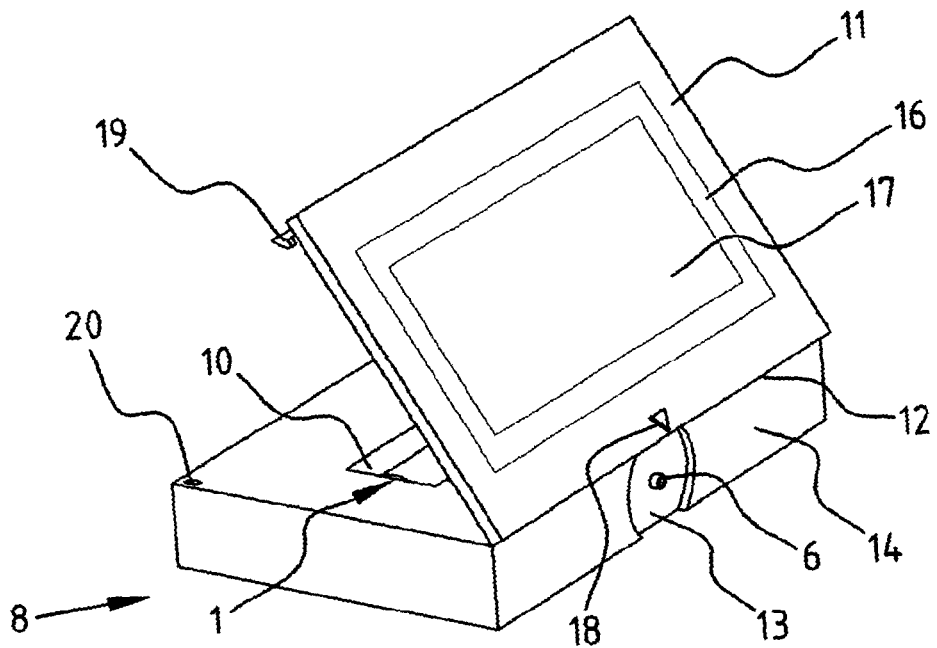
Figure 5:
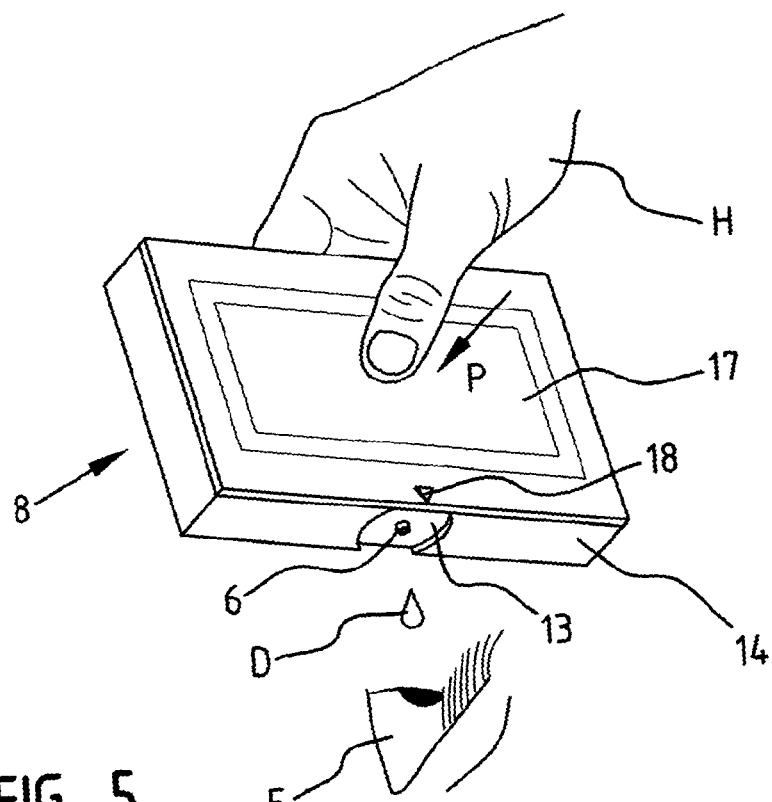
Figure 9:
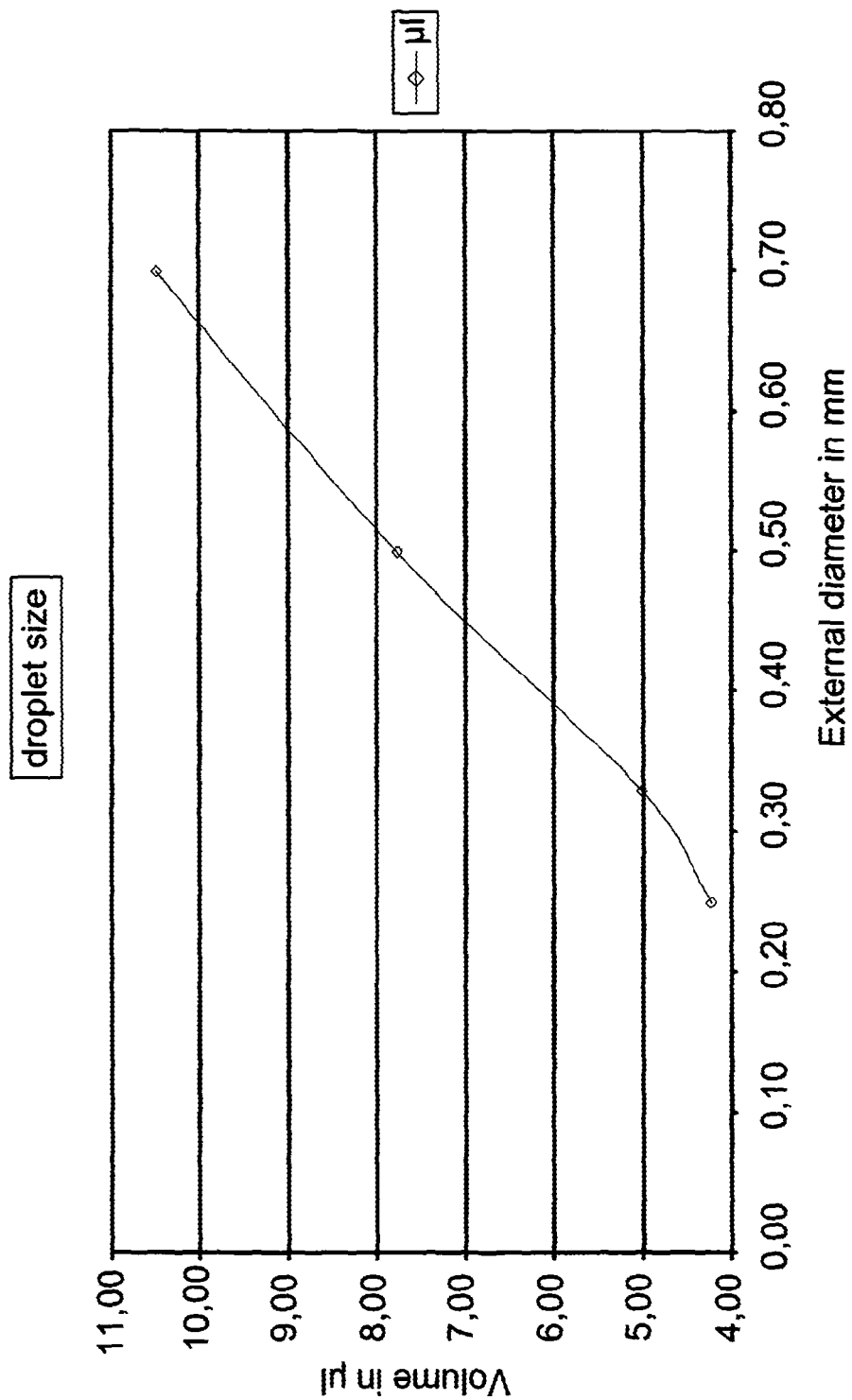

The invention is now elucidated on the basis of a number of examples, wherein reference is made to the accompanying drawing, in which:

FIGS. 1A-1C show schematic sections of the most important steps of the method according to the invention, wherein a packaging filled with liquid is opened and the liquid drips therefrom, FIG. 2 is a perspective view of an administering device according to a first embodiment of the invention at the moment when a packaging filled with liquid is placed therein, FIG. 3 is a top view of the administering device of FIG. 2 without cover, with the packaging therein, FIG. 4 is a perspective view of the administering device from a different angle, FIG. 5 is a perspective view of the device during administering of eye-drops, FIGS. 6 and 7 show respectively a front view and a side view of an alternative embodiment of the packaging, which is provided with integrated means for opening thereof, FIG. 8 is a perspective view of the packaging with opening means of FIGS. 6 and 7, and FIG. 9 shows a graph representing the relation between the external diameter of the outflow channel and the size of the dispensed drops.

A method for administering a liquid F in drops D comprises according to the invention the following steps:

a packaging 1 is provided which is wholly or partially filled with liquid F and which can be received in receiving means 2, although could in principle also be held by a user (FIG. 1A), an opening 4 is formed in packaging 1 using opening means 3 by moving opening means 3 and packaging 1 relative to each other in the direction of arrows M (FIG. 1A), and the thus formed opening 4 is connected to an outflow channel 5 which has an administering opening 6.

The forming of opening 4 takes place here in substantially pressureless manner, thereby preventing the liquid F flowing directly out of the thus formed opening. The liquid F is instead pressed out of packaging 1—which in the shown example is deformable—by exerting pressure forces P on receiving means 2. Packaging 1 is thereby deformed and liquid F flows through outflow channel 5, and this liquid F leaves administering opening 6 in the form of—preferably small—drops D (FIG. 1C) The pressure forces P which are exerted are so small that individual drops D are indeed formed, and not a jet of liquid. This is achieved when the (over)pressure in packaging 1 remains limited to less than 2 bar, and preferably even less than 1 bar.

In the shown example opening means 3 are formed by a sharp outer end of outflow channel 5, which can be manufactured from a hard plastic or metal, so that opening 4 is already connected to outflow channel 5 immediately during forming thereof. The sharp outer end of the outflow channel is pressed through wall 7 of packaging 1, which is manufactured from a semi-rigid to very flexible material with a wall thickness such that it does not begin to leak during handling thereof but can still be pierced relatively easily by opening means 3. The type of material and thickness of wall 7 of packaging 1 are further chosen such that the concentration and integrity of the liquid F remain guaranteed for a determined shelf-life thereof. In addition, the material from which packaging 1 is manufactured is chosen on the basis of its compatibility with the liquid F to be received therein.

The form, dimensions and material of outflow channel 5 and administering opening 6 are chosen such that relatively small drops D can hereby be formed. Drops D preferably have a volume of 1 to 50 µl, more preferably a volume of 2 to 25 µl and most preferably a volume of 3 to 10 µl. The precise form and dimensions of outflow channel 5 and administering opening 6 with which these drop volumes can be achieved depends on the material used and the nature of liquid F, particularly its surface tension and viscosity.

It has been found that the drop size is a function of the external diameter of the outer end of outflow channel 5 at the position of administering opening 6. This can be seen in the graph on the basis of experimental data in FIG. 9, which shows for a usual eye-drop liquid the measured volume of drops dispensed through outflow channels with different external diameters. It becomes apparent herefrom that the sought drop volumes can be achieved with outer diameters in the order of about 0.2 to 0.8 millimeters. When outflow channel 5 is manufactured from steel, channel 5 and administering opening 6 will in practice have an internal diameter in the order of magnitude of several tenths or several hundredths of a millimeter, while the wall thickness of outflow channel 5 will be in the same order of magnitude. It is for instance possible to envisage a wall thickness of 0.075 mm and an internal diameter of 0.05 mm, this combination resulting in an external diameter of 0.2 mm.

A possible embodiment of a device 8 with which liquid F can be pressed out of packaging 1 in the above described manner is shown in FIG. 2. This administering device 8 comprises a frame 9 in the form of a box in which a receiving space 10 for packaging 1 is formed. A cover 11 is connected hingedly along an edge 12 to box-like frame 9 and serves to close receiving space 10. In the shown embodiment outflow channel 5 is fixed in box-like frame 9 and protrudes with its sharp outer end 3 into receiving space 10 (FIG. 3). Outflow channel 5 extends therefrom through box-like frame 9 to a countersunk part 13 of a side wall 14 of frame 9, where it debauches into administering opening 6 (FIG. 4). The eye E is thus protected from contact with the outer end of outflow channel 5.

Because opening means 3 are here fixed relative to receiving space 10, packaging 1 must be movable into receiving space 10 to enable the forming of an opening 4 therein. For this purpose receiving space 10 is larger than the dimensions of packaging 1. In order to press packaging 1 in precisely determined manner against the sharp tip 3 of outflow channel 5, administering device 8 is provided here with a number of displacing members 15, which can be carried into receiving space 10 and there engage on packaging 1. These displacing members 15 here take the form of wedge-like protrusions on the inner side of cover 11 which, when cover 11 is closed, penetrate into receiving space 10 and there press packaging 1 against opening means 3 (shown with broken lines in FIG. 3), whereby opening 4 is formed.

It would of course also be possible to envisage the packaging 1 being fixed in receiving space 10 and opening means 3 being mounted movably in frame 9. These opening means 3 could then for instance be pressed against packaging 1 when cover 11 is closed. Other combinations of movements of packaging 1 and opening means 3 can also be envisaged.

Further formed on cover 11 are two hooks 19 which drop into openings 20 in box-like frame 9 when cover 11 is closed. Cover 11 is hereby fixed and packaging 1 is permanently enclosed in receiving space 10, so that administering device 8 cannot be reused. Other solutions can of course also be envisaged to make reuse of device 8 impossible, such as making the outflow channel unusable or damaging a label with which device 8 is sealed.

Once opening 4 has been formed in packaging 1 by closing the cover 11, device 8 is ready for use, this being indicated by the audible and feelable click with which hooks 19 of cover 11 are clicked into openings 20. The liquid F can then be pressed out of packaging 1. In the shown example the cover 11, or at least the part thereof closing receiving space 10, is for this purpose deformable. Cover 11 can thus be pressed and pressure can thereby be exerted on deformable packaging 1. The resistance of cover 11 to deformation forms a resistance which gives the user an impression of how dosing of the drops is progressing. In order to prevent the pressure force on packaging 1 being discontinued when cover 11 is released, the latter is preferably plastically deformable so that it retains its deformation. Cover 11 is embodied such that the maximum deformation is reached at the moment packaging 1 is still partially filled with liquid F. Use can thus be made during the whole of the administration of liquid pressure in packaging 1 in order to urge the drops outward through administering opening 6.

Instead of having a deformable wall part, the receiving space 10 could also have a displaceable part with which the pressure force could be exerted on packaging 1. The resistance could in this case be generated for instance by one or more springs. In order to prevent reverse movement a one-way locking, for instance in the manner of ratchet teeth or a tie-wrap, could then be applied. Passing over a ratchet tooth, which will be accompanied by a feelable and audible click, could then correspond in each case to the administering of a single drop. A clear indication is thus given of the administering progress, wherein the user can keep track of the number of drops administered on the basis of the number of clicks. The end of administration could then be defined by a stop.

As clearly shown, the dimensions of administering device 8 are considerably larger than those of packaging 1. Device 8 is hereby easier to handle than packaging 1, this being particularly advantageous for older users. A space 16 on which an information carrier 17 can be arranged is moreover thus defined on cover 11 (FIG. 4). Information can be printed thereon relating to the composition of the liquid and the manner in which and the regularity with which it must be administered. Further arranged on cover 11 is a mark 18 indicating the location of administering opening 6, which does not after all protrude outside the periphery of device 8.

Prior to use both packaging 1 and administering device 8 can be sterilized, either individually or after packaging 1 has already been placed in receiving space 10. In order to guarantee sterility the administering opening 6 can be provided with a closure which is removed during use. Once packaging 1 has been placed in receiving space 10 and cover 11 has been closed, whereby opening 4 is formed in packaging 1, the user takes device 8 in the hand H and holds it above his/her eye E (FIG. 5). By now exerting pressure on the top and bottom side of the device the liquid F is pressed out of packaging 1 through outflow channel 5 and dispensed through administering opening 6 in the form of drops D. These drops D fall into the eye E. When the desired quantity of drops D has been administered, this is indicated by a sudden strongly increasing resistance and/or by an audible or visible signal. The user can subsequently discard or hand in at a collection point the device 8 having enclosed therein the packaging still partially filled with liquid F.

In an alternative embodiment of the invention opening means 3 are not received in a frame but are connected to packaging 1 (FIG. 6-8). Opening means 3 are here once again formed by the sharp tip of an outflow channel 5 which defines an administering opening 6 at its opposite end. In this embodiment outflow channel 5 is received in a displacing member 15 connected via two film hinges 21 to packaging 1. Displacing member 15 here has two protruding parts 22 between which the end of outflow channel 5 debouches. In this embodiment, where opening means 3 and outflow channel 5 are formed integrally with packaging 1, administering device 8 can be embodied in particularly simple manner. This device 8 need in fact comprise, in addition to the shown components, not much more than a stop against which the protruding parts 22 of displacing member 15 can be pressed. Film hinges 21 will hereby be folded shut and the sharp outer end 3 of outflow channel 5 will pierce the wall of packaging 1 in order to open packaging 1. Liquid drops D can then be pressed out of packaging 1 simply by squeezing packaging 1.

It is even possible in this embodiment to envisage packaging 1, displacing member 15 and outflow channel 5 with sharp tip 3 and administering opening 6 together forming the whole administering device. A user can hold packaging 1 and displacing member 15 in the hand and move them toward each other, whereby packaging 1 is opened, and then carefully squeeze packaging 1 in order to dispense liquid drops D.

Although the invention is elucidated above on the basis of a number of embodiments, it will be apparent that it is not limited thereto. The receiving means and the opening means could thus be embodied other than shown here. The packaging could also be embodied differently, and could even be integrated into the administering device. Additional provisions could further be incorporated in the administering device. This could for instance have a safeguard against the packaging unintentionally being pressed empty prematurely. The device could also be embodied such that the dosage of the drops does not depend, or hardly so, on the force exerted by the user.

The scope of the invention is therefore defined solely by the following claims.

The invention claimed is:

1. A method for administering a liquid drop by drop, comprising the steps of:
   supplying a deformable packaging at least partially filled with the liquid;
   forming at least one opening in the packaging in a substantially pressureless manner by using an opener, wherein the opening is formed by moving the opener and the packaging relative to each other;
   connecting the at least one opening to at least one outflow channel which has an administering opening; and
   pressing the liquid from the deformable packaging by manually exerting a pressing force such that the liquid is delivered drop by drop, characterized in that the liquid is pressed out of the packaging at a pressure of a maximum of 2 bar.

2. The method as claimed in claim 1, characterized in that the packaging is received and fixed in a receptacle and the opener is moved toward the packaging.

3. The method as claimed in claim 1, characterized in that the packaging is received in a receptacle, the opener is fixed relative to the receptacle and the packaging is moved toward the opener.

4. The method as claimed in claim 1, characterized in that the packaging is placed in a receiving space of the receptacle and the liquid is pressed therefrom by exerting a pressing force on a movable or deformable wall part of the receiving space.

5. A method for administering a liquid drop by drop, comprising the steps of:
   supplying a packaging at least partially filled with the liquid;
   forming at least one opening in the packaging using an opener; and
   connecting the at least one opening to at least one outflow channel which has an administering opening, wherein the opening is formed by moving the opener and the packaging relative to each other, characterized in that the packaging is deformable and the liquid is pressed out of the packaging at a pressure of a maximum of 2 bar.

6. The method as claimed in claim 5, characterized in that the liquid is pressed out of the packaging at a pressure of a maximum of 1 bar.

7. A device for administering a liquid drop by drop, comprising a packaging at least partially filled with the liquid, at least one outflow channel with an administering opening, and an opener connected to the at least one outflow channel for opening the packaging, wherein the opener and the packaging are movable relative to each other,
   characterized in that the packaging is deformable and there is a pressing member for exerting pressure on the packaging,
   wherein the pressing member is arranged for exerting a pressure of a maximum of 2 bar on the packaging.

8. The administering device as claimed in claim 7, wherein the pressing member is arranged for exerting a pressure of a maximum of 1 bar on the packaging.

9. A method for administering a liquid drop by drop, comprising the steps of:
- supplying a deformable packaging at least partially filled with the liquid;
- forming at least one opening in the packaging in a substantially pressureless manner by using an opener, wherein the opening is formed by moving the opener and the packaging relative to each other;
- connecting the at least one opening to at least one outflow channel which has an administering opening; and
- pressing the liquid from the deformable packaging by manually exerting a pressing force such that the liquid is delivered drop by drop, wherein the liquid is pressed out of the packaging at a pressure of a maximum of 1 bar.

10. The method as claimed in claim 1, wherein the liquid is administered in drops with a volume of 2 to 25 μl.

11. The method as claimed in claim 10, wherein the liquid is administered in drops with a volume of 3 to 10 μl.

12. The method as claimed in claim 11, wherein the liquid is administered in drops with a volume of 5 to 7 μl.

13. The method as claimed in claim 9, characterized in that the packaging is received and fixed in a receptacle and the opener is moved toward the packaging.

14. The method as claimed in claim 9, characterized in that the packaging is received in a receptacle, the opener is fixed relative to the receptacle and the packaging is moved toward the opener.

15. The method as claimed in claim 9, characterized in that the packaging is placed in a receiving space of the receptacle and the liquid is pressed therefrom by exerting a pressing force on a movable or deformable wall part of the receiving space.

16. The method as claimed in claim 9, wherein the liquid is administered in drops with a volume of 2 to 25 μl.

17. The method as claimed in claim 16, wherein the liquid is administered in drops with a volume of 3 to 10 μl.

18. The method as claimed in claim 17, wherein the liquid is administered in drops with a volume of 5 to 7 μl.

* * * * *